(12) United States Patent
Johnson et al.

(10) Patent No.: US 9,079,816 B2
(45) Date of Patent: Jul. 14, 2015

(54) PROCESS FOR PRODUCING ALKYLATED AROMATIC COMPOUNDS

(71) Applicant: UOP LLC, Des Plaines, IL (US)

(72) Inventors: James A. Johnson, Burr Ridge, IL (US); Paul T. Barger, Arlington Heights, IL (US); Maureen L. Bricker, Buffalo Grove, IL (US); John Q. Chen, Glenview, IL (US); Peter K. Coughlin, Mundelein, IL (US); Stanley J. Frey, Palatine, IL (US); Joseph A. Kocal, Glenview, IL (US); Matthew Lippmann, Chicago, IL (US); Vasant P. Thakkar, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/466,660

(22) Filed: Aug. 22, 2014

(65) Prior Publication Data

US 2015/0141700 A1    May 21, 2015

Related U.S. Application Data

(60) Provisional application No. 61/906,069, filed on Nov. 19, 2013.

(51) Int. Cl.
| | |
|---|---|
| *C07C 45/53* | (2006.01) |
| *C07C 2/66* | (2006.01) |
| *C07C 5/22* | (2006.01) |
| *C07C 37/08* | (2006.01) |
| *C07C 37/00* | (2006.01) |
| *C07C 7/10* | (2006.01) |
| *C07C 6/06* | (2006.01) |

(52) U.S. Cl.
CPC ... *C07C 2/66* (2013.01); *C07C 5/22* (2013.01); *C07C 6/06* (2013.01); *C07C 7/10* (2013.01); *C07C 37/00* (2013.01); *C07C 37/08* (2013.01); *C07C 45/53* (2013.01)

(58) Field of Classification Search
CPC ............ C07C 45/53; C07C 37/08; C07C 2/66
USPC ........................... 568/397, 768; 585/323, 446
See application file for complete search history.

(56) References Cited

U.S. PATENT DOCUMENTS

| | | | |
|---|---|---|---|
| 8,246,815 B2 | 8/2012 | Wu et al. | |
| 2009/0288985 A1 | 11/2009 | Long et al. | |
| 2013/0228447 A1 | 9/2013 | Wu et al. | |

FOREIGN PATENT DOCUMENTS

| | | |
|---|---|---|
| CN | 1718685 A | 1/2006 |
| CN | 101531558 A | 9/2009 |
| GB | 625505 | 6/1949 |
| GB | 2396610 A | 6/2004 |

OTHER PUBLICATIONS

Sweeney et al., "BTX Processing," Kirk-Othmer Encyclopedia of Chemical Technology, Chevron Research and Technology Company, Published online Dec. 14, 2001, 1-17.

Broughton et al., "Production of High Purity Aromatics by the Sulfolane Process," Seventh World Petroleum Congress—vol. 4: Refining, Elsevier Publishing (1967), 65-73.

*Primary Examiner* — Sikarl Whiterspoon

(57) ABSTRACT

A process for producing alkylated aromatic compounds includes pyrolyzing a coal feed to produce a coke stream and a coal tar stream. The coal tar stream is hydrotreated and the resulting hydrotreated coal tar stream is cracked. A portion of the cracked coal tar stream is separated to obtain a fraction having an initial boiling point in the range of about 60° C. to about 180° C., and an aromatics-rich hydrocarbon stream is extracted by contacting the fraction with one or more solvents. The aromatics-rich hydrocarbon stream is contacted with an alkylating agent to produce an alkylated aromatic stream, or the aromatics-rich hydrocarbon stream is reacted with an aliphatic compound or methanol in the presence of a catalyst to produce a methylated aromatic stream. The alkylated aromatic stream, the methylated aromatic stream, or both are separated into at least a benzene stream, a toluene stream, and a xylenes stream.

20 Claims, 2 Drawing Sheets

PROCESS FOR PRODUCING ALKYLATED AROMATIC COMPOUNDS

RELATED APPLICATIONS

This application claims priority to U.S. Provisional Application. No. 61/906,069 filed on Nov. 19, 2013, the entirety of which is incorporated herein by reference.

BACKGROUND OF THE INVENTION

Many different types of chemicals are produced from the processing of petroleum. However, petroleum is becoming more expensive because of increased demand in recent decades.

Therefore, attempts have been made to provide alternative sources for the starting materials for manufacturing chemicals. Attention is now being focused on producing liquid hydrocarbons from solid carbonaceous materials, such as coal, which is available in large quantities in countries such as the United States and China.

Pyrolysis of coal produces coke and coal tar. The coke-making or "coking" process consists of heating the material in closed vessels in the absence of oxygen to very high temperatures. Coke is a porous but hard residue that is mostly carbon and inorganic ash, which may be used in making steel.

Coal tar is the volatile material that is driven off during heating, and it comprises a mixture of a number of hydrocarbon compounds. It can be separated to yield a variety of organic compounds, such as benzene, toluene, xylene, naphthalene, anthracene, and phenanthrene. These organic compounds can be used to make numerous products, for example, dyes, drugs, explosives, flavorings, perfumes, preservatives, synthetic resins, and paints and stains. The residual pitch left from the separation is used for paving, roofing, waterproofing, and insulation.

These organic compounds, and particularly alkylated aromatic compounds, are relatively high value. Thus, there is a need for an improved process for producing alkylated aromatic compounds from coal tar.

SUMMARY OF THE INVENTION

In a first aspect, a process for producing alkylated aromatic compounds includes pyrolyzing a coal feed to produce a coke stream and a coal tar stream. The coal tar stream is hydrotreated and the resulting hydrotreated coal tar stream is cracked. The process further includes separating a portion of the cracked coal tar stream to obtain a fraction having an initial boiling point in the range of about 60° C. to about 180° C., and extracting an aromatics-rich hydrocarbon stream by contacting the fraction with one or more solvents. The aromatics-rich hydrocarbon stream is contacted with an alkylating agent in the presence of an alkylation catalyst in an alkylation zone to produce an alkylated aromatic stream, or the aromatics-rich hydrocarbon stream with an aliphatic compound or methanol in the presence of a methylation catalyst in a methylation zone to produce a methylated aromatic stream. The alkylated aromatic stream, the methylated aromatic stream, or both are separated into at least a benzene stream, a toluene stream, and a xylenes stream.

In another aspect, a process for producing alkylated aromatic compounds includes pyrolyzing a coal feed to produce a coke stream and a coal tar stream. The coal tar stream is hydrotreated and the resulting hydrotreated coal tar stream is cracked. The process further includes separating a portion of the cracked coal tar stream to obtain a fraction having an initial boiling point in the range of about 60° C. to about 180° C., and extracting an aromatics-rich hydrocarbon stream by contacting the fraction with one or more solvents. The process further includes contacting the aromatics-rich hydrocarbon stream with an alkylating agent in the presence of an alkylation catalyst in an alkylation zone to produce an alkylated aromatic stream, or contacting the aromatics-rich hydrocarbon stream with an aliphatic compound or methanol in the presence of a methylation catalyst in a methylation zone to produce a methylated aromatic stream, and separating the alkylated aromatic stream into at least a first stream comprising ethyl benzene and diethyl benzenes, a second stream comprising cumenes and di-isopropyl benzenes, and a third stream comprising cymenes and di-isopropyl toluenes in a separation zone.

DETAILED DESCRIPTION OF THE INVENTION

Figure 1:
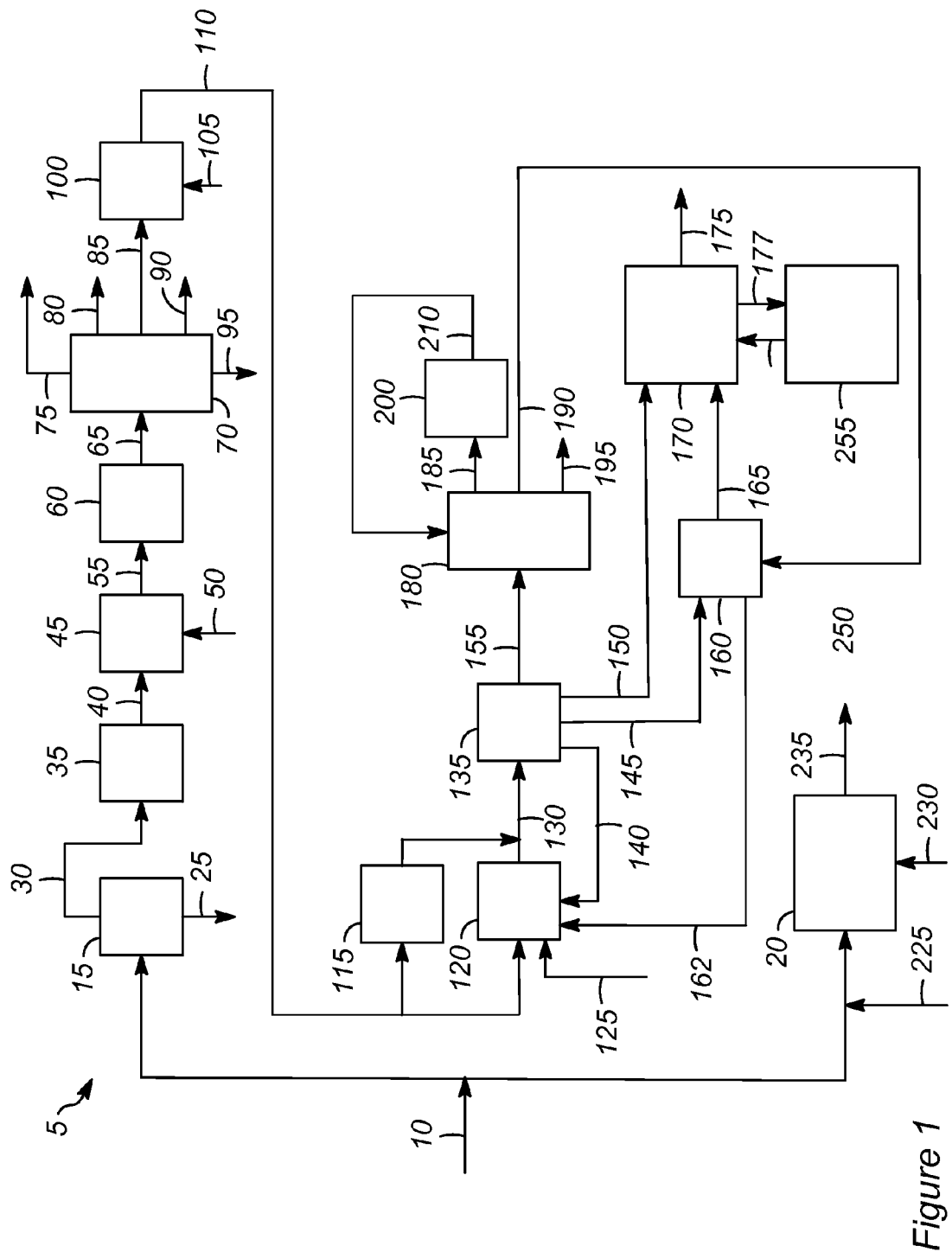
FIG. 1 is an illustration of one embodiment of a process of the present invention.

FIG. 1 shows one embodiment of a basic coal conversion process 5. A coal feed 10 can be sent to a pyrolysis zone 15 such as a coking oven zone, a gasification zone 20, or the coal feed 10 can be split into two parts and sent to both.

In the pyrolysis zone 15, the coal is heated at high temperature, e.g., up to about 2,000° C. (3,600° F.), in the absence of oxygen to drive off the volatile components. Coking produces a coke stream 25 and a coal tar stream 30. The coke stream 25 can be used in other processes, such as the manufacture of steel.

The coal tar stream 30, which comprises the volatile components from the coking process, can be sent to an optional contamination removal zone 35, if desired.

While the contaminant removal zone 35 is shown immediately downstream from the pyrolysis zone 15 in FIG. 1, those of skill in the art will recognize that the contaminant removal zone 35 for removing one or more contaminants from the coal tar stream or another process stream may be located at various positions along the process depending on the impact of the particular contaminant on the product or process and the reason for the contaminant's removal, as described further below. For example, the contaminant removal zone 35 can be positioned upstream of a separation zone 70. Some contaminants have been identified to interfere with a downstream processing step or hydrocarbon conversion process, in which case the contaminant removal zone 35 may be positioned upstream of the separation zone 70 or between the separation zone 70 and the particular downstream processing step at issue. Still other contaminants have been identified that should be removed to meet particular product specifications. Where it is desired to remove multiple contaminants from the hydrocarbon or process stream, multiple contaminant removal zones may be positioned at different locations along the process. In still other approaches, a contaminant removal zone 35 may overlap or be integrated with another process within the system, in which case the contaminant may be removed during another portion of the process, including, but not limited to the separation zone 70 or the downstream hydrocarbon conversion zone. This may be accomplished with or without modification to these particular zones, reactors or processes. While the contaminant removal zone 35 is often positioned downstream of the hydrocarbon conversion reactor, it should be understood that the contaminant removal zone in accordance herewith may be positioned upstream of the separation zone 70, between the separation zone 70 and the hydrocarbon conversion zone, downstream of the hydrocarbon conversion zone, or along other streams within the process stream, such as, for example, a carrier fluid stream, a fuel stream, an oxygen source stream, or any streams used in the systems and the processes described herein. The contaminant concentration is controlled by removing at least a portion of the contaminant from the stream. As used herein, the term "removing" may refer to actual removal, for example by adsorption, absorption, or membrane separation, or it may refer to conversion of the contaminant to a more tolerable compound, or both.

A decontaminated coal tar feed 40 is sent to a hydrotreating zone 45. Hydrotreating is a process in which hydrogen gas 50 is contacted with a hydrocarbon stream in the presence of one or more suitable catalysts, which are primarily active for the removal of heteroatoms, such as sulfur, nitrogen, oxygen, and metals from the hydrocarbon feedstock. In hydrotreating, hydrocarbons with double and triple bonds may be saturated. Aromatics may also be saturated. Typical hydrotreating reaction conditions include a temperature of about 290° C. (550° F.) to about 455° C. (850° F.), a pressure of about 3.4 MPa (500 psig) to about 27.6 MPa (4,000 psig), a liquid hourly space velocity of about 0.5 $hr^{-1}$ to about 4 $hr^{-1}$, and a hydrogen rate of about 168 to about 1,011 $Nm^3/m^3$ oil (1,000-6,000 scf/bbl). Typical hydrotreating catalysts include at least one Group VIII metal, preferably iron, cobalt and nickel, and at least one Group VI metal, preferably molybdenum and tungsten, on a high surface area support material, preferably alumina. Other typical hydrotreating catalysts include zeolitic catalysts, as well as noble metal catalysts where the noble metal is selected from palladium and platinum.

After hydrotreating, a hydrotreated coal tar stream 55 enters a cracking zone 60. Broadly, heavy hydrocarbons entering the cracking zone 60 are broken into simpler molecules such as lighter hydrocarbons by breaking carbon-carbon bonds within the hydrocarbon molecule. In particular, the cracking zone 60 is preferably a catalytic cracking zone comprising, for example, one or more of a hydrocracking zone and a fluid catalytic cracking zone.

Hydrocracking is a process in which hydrocarbons crack in the presence of hydrogen to lower molecular weight hydrocarbons. Typical hydrocracking conditions may include a temperature of about 290° C. (550° F.) to about 468° C. (875° F.), a pressure of about 3.5 MPa (500 psig) to about 20.7 MPa (3,000 psig), a liquid hourly space velocity (LHSV) of about 1.0 to less than about 2.5 $hr^{-1}$, and a hydrogen rate of about 421 to about 2,527 $Nm^3/m^3$ oil (2,500-15,000 scf/bbl). Typical hydrocracking catalysts include amorphous silica-alumina bases or low-level zeolite bases combined with one or more Group VIII or Group VIB metal hydrogenating components, or a crystalline zeolite cracking base upon which is deposited a Group VIII metal hydrogenating component. Additional hydrogenating components may be selected from Group VIB for incorporation with the zeolite base.

Fluid catalytic cracking (FCC) is a catalytic hydrocarbon conversion process accomplished by contacting heavier hydrocarbons in a fluidized reaction zone with a catalytic particulate material. The reaction in catalytic cracking is carried out in the absence of substantial added hydrogen or the consumption of hydrogen. The process typically employs a powdered catalyst having the particles suspended in a rising flow of feed hydrocarbons to form a fluidized bed. In representative processes, cracking takes place in a riser, which is a vertical or upward sloped pipe. Typically, a pre-heated feed is sprayed into the base of the riser via feed nozzles where it contacts hot fluidized catalyst and is vaporized on contact with the catalyst, and the cracking occurs converting the high molecular weight oil into lighter components including liquefied petroleum gas (LPG), gasoline, and a distillate. The catalyst-feed mixture flows upward through the riser for a short period (a few seconds), and then the mixture is separated in cyclones. The hydrocarbons are directed to a fractionator for separation into LPG, gasoline, diesel, kerosene, jet fuel, and other possible fractions. While going through the riser, the cracking catalyst is deactivated because the process is accompanied by formation of coke which deposits on the catalyst particles. Contaminated catalyst is separated from the cracked hydrocarbon vapors and is further treated with steam to remove hydrocarbon remaining in the pores of the catalyst. The catalyst is then directed into a regenerator where the coke is burned off the surface of the catalyst particles, thus restoring the catalyst's activity and providing the necessary heat for the next reaction cycle. The process of cracking is endothermic. The regenerated catalyst is then used in the new cycle. Typical FCC conditions include a temperature of about 400° C. to about 800° C., a pressure of about 0 to about 688 kPag (about 0 to 100 psig), and contact times of about 0.1 seconds to about 1 hour. The conditions are determined based on the hydrocarbon feedstock being cracked, and the cracked products desired. Zeolite-based catalysts are commonly used in FCC reactors, as are composite catalysts which contain zeolites, silica-aluminas, alumina, and other binders.

A cracked hydrocarbon stream 65 then enters a separation zone 70, where the cracked stream 65 is separated into two or more fractions 75, 80, 85, 90, 95. Hydrotreated and cracked coal tar stream 65 comprises a complex mixture of heterocyclic aromatic compounds and their derivatives with a wide range of boiling points. The number of fractions and the components in the various fractions can be varied as is well known in the art. A typical separation process involves separating the cracked stream 65 into four to six streams. For example, there can be a fraction comprising $NH_3$, CO, and light hydrocarbons, a light oil fraction with boiling points between 0° C. and 180° C., a middle oil fraction with boiling points between 180° C. to 230° C., a heavy oil fraction with boiling points between 230 to 270° C., an anthracene oil fraction with boiling points between 270° C. to 350° C., and pitch. Suitable separation processes include, but are not limited to fractionation, solvent extraction or adsorption.

The light oil fraction contains compounds such as benzene, toluene, xylenes, naphtha, coumarone-indene, dicyclopentadiene, pyridine, and picoline. The middle oil fraction contains compounds such as phenols, cresols and cresylic acids, xylenols, naphthalene, high boiling tar acids, and high boiling tar bases. The heavy oil fraction contains creosotes. The anthracene oil fraction contains anthracene. Pitch is the residue of the hydrotreated and cracked coal tar distillation containing primarily aromatic hydrocarbons and heterocyclic compounds.

As illustrated, the hydrotreated and cracked feed 65 is separated into a gas fraction 75 containing gases such as $NH_3$ and CO as well as light hydrocarbons, such as ethane, hydrocarbon fractions 80, 85, and 90 having different initial boiling point ranges, and pitch fraction 95. One or more of the fractions 75, 80, 85, 90, and 95 can be further processed, as desired.

As illustrated, a fraction 85 can be sent to an extraction zone 100. The fraction 85 is a relatively light stream having an initial boiling point that is preferably in the range of about 60° C. to about 180° C. In the extraction zone 100, the fraction 85 is preferably contacted with one or more liquid solvents 105, including one or more of sulfolane, an organic ether of sulfolane, N-methyl-2-pyrrolidone (NMP), and N-methylformamide (NMF). The extraction process includes subjecting the fraction 85 to one or more of liquid-liquid extraction or extractive distillation to produce a raffinate (not shown) and an aromatics-rich hydrocarbon stream 110 including concentrations of benzene, toluene, and xylenes, and $C_{9+}$ aromatic hydrocarbons.

An aromatics-rich hydrocarbon stream 110 then flows to an alkylation zone 115. Alkylation may be performed on the stream 110 as a whole as illustrated. Alternatively, the stream 110 may be distilled to separate benzene and toluene from heavier $C_{8+}$ hydrocarbons. The benzene and toluene can then be alkylated separately. For petrochemicals, the alkylation reaction can be performed using an aromatic compound such as benzene or toluene. When using benzene and alkylating with a light olefin such as ethylene or propylene, the product is typically ethylbenzene or cumene. These can be converted to styrene or phenol plus acetone. When toluene is alkylated with propylene, cymene isomers can be produced, which could be converted into cresols. Aromatic alkylation is generally conducted with solid acid catalysts including zeolites or amorphous silica-aluminas, but can also be conducted using ionic liquid catalysts. For alkylation of aromatic compounds with light olefins, the temperature range is about from 100° C. to about 250° C. at the pressure range of about 200 to about 7,100 kPa, in liquid phase. Vapor phase alkylation could also be used, requiring a higher temperature range.

The aromatics-rich hydrocarbon stream 110 can also be routed to a methylation zone 120 in place of or in addition to the alkylation zone 115. In the methylation zone 120, the aromatics-rich hydrocarbon stream 110 is contacted with an alkylating agent 125, such as an aliphatic compound or methanol, in the presence of a methylation catalyst. The methylation catalyst is preferably a zeolite catalyst, and more preferably an MFI catalyst such as a ZSM-5 catalyst. This produces a conversion product 130 including an increased concentration of methylaromatics, including toluene, and xylenes.

The conversion product 130 then enters a distillation zone 135, which distills the conversion product 130 to separate the product into at least benzene stream 140, a toluene stream 145, and a xylenes stream 150. As shown in FIG. 1, the distillation may further separate a C9+ aromatics stream 155. The benzene stream 140 is recycled to the methylation zone 120, as illustrated in FIG. 1. Alternatively, the benzene stream 140 can be recycled to the alkylation zone 115. If methanol is used as the alkylating agent, the toluene stream 145 can also be recycled back to the methylation zone 120.

The toluene stream 145 is sent to a toluene processing zone 160. Toluene processing preferably includes one or more of methylation and disproportionation to produce a mixture of benzene and xylenes. Alternatively, the toluene could be co-processed with heavy aromatic hydrocarbon compounds such as trimethylbenzenes and methyl-ethylbenzenes (i.e., $A_{9+}$ aromatics) in a transalkylation process to produce benzene and xylenes. Toluene methylation in the toluene processing zone 160 requires contacting the toluene stream 145 with a methylating catalyst to produce a product containing benzene and xylenes.

Alternatively, the toluene processing zone 160 comprises a toluene disproportionation or, if combined with $A_{9+}$ aromatics, a transalkyaltion zone. Transalkylation is a chemical reaction resulting in transfer of an alkyl group from one organic compound to another. Catalysts, particularly zeolite catalysts, are often used to effect the reaction. If desired, the transalkylation catalyst may be metal stabilized using a noble metal or base metal, and may contain suitable binder or matrix material such as inorganic oxides and other suitable materials. In a transalkylation process, a polyalkylaromatic hydrocarbon feed and an aromatic hydrocarbon feed are provided to a transalkylation reaction zone. In the case of toluene transalkyaltion, the polyalkylaromatic hydrocarbon feed (e.g., the $C_{9+}$ stream 155) preferably includes trimethylbenzene, although other polyalkylaromatics may be used without departing from the scope of the process. The aromatic feed is the toluene stream 145. The aromatic feed and the polyalkylaromatic feed are combined and heated to reaction temperature and then passed through a reaction zone, which may comprise one or more individual reactors. Passage of the combined feed through the reaction zone produces an effluent stream comprising unconverted feed and a product containing at least benzene and additional xylenes as output. The effluent is normally cooled and passed to a stripping column in which substantially all $C_5$ and lighter hydrocarbons present in the effluent are concentrated into an overhead stream and removed from the process.

The transalkylation reaction can be effected in contact with a catalytic composite in any conventional or otherwise convenient manner and may comprise a batch or continuous type of operation, with a continuous operation being preferred. The transalkylation catalyst is usefully disposed as a fixed bed in a reaction zone of a vertical tubular reactor, with the alkylaromatic feed stock charged through the bed in an upflow or downflow manner. The transalkylation zone normally operates at conditions including a temperature in the range of about 130° C. to about 540° C. The transalkylation zone is typically operated at moderately elevated pressures broadly ranging from about 100 kPa to about 10 MPa absolute. The transalkylation reaction can be effected over a wide range of space velocities. That is, volume of charge per volume of catalyst per hour; weight hourly space velocity (WHSV) generally is in the range of from about 0.1 to about 30 $hr^{-1}$. The catalyst is typically selected to have relatively high stability at a high activity level.

The toluene processing zone 160 preferably further includes a separator to separate the product of the methylation, transalkylation, or disproportionation reaction into at least a benzene stream 162 and a xylenes stream 165. The benzene stream 162 is recycled to the methylation zone 120 as shown in FIG. 1. Alternatively, the benzene stream 162 could be routed to the alkylation zone 115.

The xylenes product stream 165 from the toluene processing zone 160 and the xylenes stream 150 from the distillation zone 135 are routed to a xylene isomer recovery zone 170. In the xylene isomer recovery zone 170, the mixed xylenes from xylenes streams 150, 165 are purified to recover one or more purified streams 175 of para-xylene, meta-xylene, and/or ortho-xylene. Para-xylene and meta-xylene can be recovered using adsorption process, and ortho-xylene can be recovered using distillation.

The remainder isomer stream 177, comprising the unrecovered xylene isomers, is routed to an isomerization zone 250. The isomerization zone 250 can be controlled to isomerize the remaining xylenes back to an equilibrium mixture 255 which can be returned to the xylene isomer recovery zone 170.

In some embodiments, the $C_{9+}$ aromatics stream 155 from the distillation zone 135 is routed to a second separation zone 180. The $C_{9+}$ aromatics stream 155 comprises aromatic hydrocarbon compounds having 9 or more carbon atoms, and having a range of initial boiling points. The separation zone 180 separates the contents of the aromatics stream 155 based on their boiling points, with the lightest ones being n-propyl benzene, iso-propyl benzene and the isomers of methyl ethyl benzene. These relatively volatile aromatics can be separated from the tri-methyl benzene and heavier components. As shown in FIG. 1, the $C_{9+}$ aromatics stream 155 is separated into three streams 185, 190, and 195, although it will be appreciated that the stream 155 may be separated into more or fewer streams, as desired.

Each of the product streams 185, 190, 195 can be subject to downstream processing as desired. In particular, the product stream 185 comprising the most volatile of the $C_9$ aromatic isomers articulated above is routed to an aromatics conversion zone 200 where it is contacted with a platinum-containing catalyst to convert at least a portion of the $C_9$ aromatics to trimethylbenzenes, thereby producing a product stream 210 having an increased concentration of trimethylbenzenes. The trimethylbenzene-rich stream 210 is then recycled to the second separation zone 180. Additionally, one or more of the product streams 190 and 195, which are the medium and heavy portions of the $C_9+$ aromatics, can be routed to the toluene processing zone 160 for transalkylation. That is, while FIG. 1 shows only product stream 190 being recycled to the toluene processing zone 160, it will be appreciated by those of skill in the art that product stream 195 may be routed to the toluene processing zone 160 in place of or in addition to product stream 190.

In some processes, all or a portion of the coal feed 10 is mixed with oxygen 225 and steam 230 and reacted under heat and pressure in the gasification zone 20 to form syngas 235, which is a mixture of carbon monoxide and hydrogen. The syngas 235 can be further processed using the Fischer-Tropsch reaction to produce gasoline or using the water-gas shift reaction to produce more hydrogen.

Figure 2:
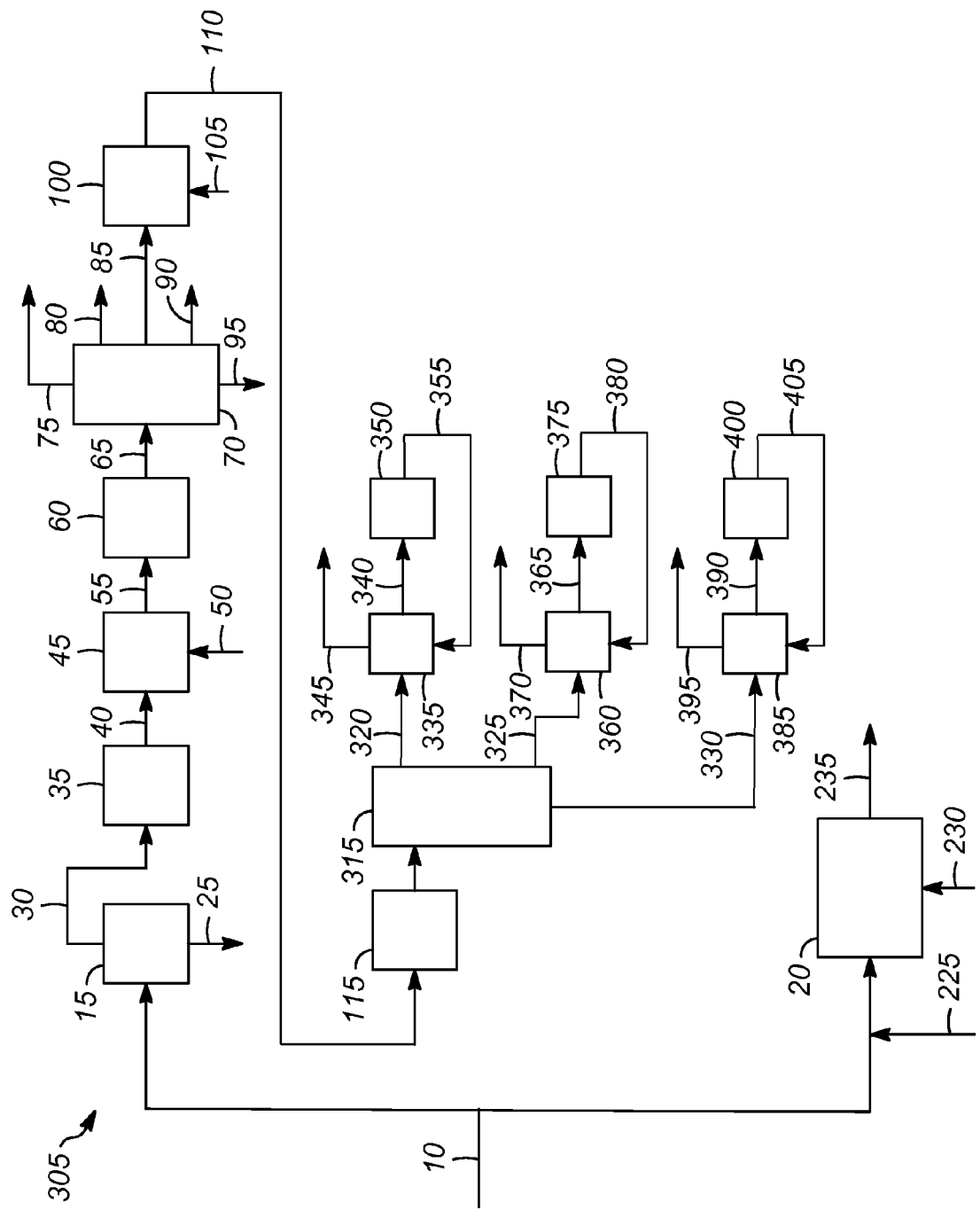
FIG. 2 is an illustration of another embodiment of a process of the present invention.

FIG. 2 shows an alternate embodiment of a basic coal conversion process, generally labeled 305, for use if the desired end product is one or more of ethylbenzene, styrene, cumene, phenol, cymene, or cresols. The process is similar to the process 5 described above in FIG. 1, and like elements are given identical reference numbers to aid understanding. An aromatics-rich hydrocarbon stream 110 is provided to alkylation zone 115 for alkylation processing. The alkylation reaction can be performed using an aromatic compound such as benzene or toluene. When using benzene and alkylating with a light olefin such as ethylene or propylene, the product is typically ethylbenzene or cumene. These can be converted to styrene or phenol plus acetone. When toluene is alkylated with propylene, cymene isomers can be produced, which could be converted into cresols.

The output of the alkylation zone 115, is provided to a distillation section 315 for separation into multiple component streams. The distillation section 315 separates the alkylated aromatics into three separate product streams 320, 325, 330. It will be appreciated that more or fewer streams could be separated without departing from the scope of the invention. A first of the product streams 320 includes ethylbenzene and diethylbenzene; a second product stream 325 includes at least cumene and di-isopropylbenzene; a third product 330 stream includes at least cymenes and di-isopropyl toluene isomers.

The first stream 320 enters a first separation zone 335 to separate the stream 320 into at least a diethylbenzene stream 340 and an ethylbenzene stream 345. The diethylbenzene stream 340 is provided to a first transalkylation zone 350 to transalkylate at least a portion of the diethylbenzene with pure benzene in the presence of a transalkylation catalyst, forming an ethylbenzene product stream 355. The ethylbenzene product stream 355 is then recycled to the first separation zone 335.

The ethylbenzene stream 345 can be collected as a final product, or optionally subjected to further downstream processing. For example, the ethylbenzene stream 345 could be subjected to an isomerization process to produce xylenes from the ethylbenzene, if desired. Alternatively, the ethylbenzene could be converted to other useful products such as styrene.

The second stream 325 enters a second separation zone 360 to separate the second stream 325 into at least a di-isopropylbenzene stream 365 and a cumene stream 370. The di-isopropylbenzene stream 365 is provided to a second transalkylation zone 375 to transalkylate at least a portion of the di-isopropyl benzene with pure benzene in the presence of a transalkylation catalyst, forming a cumene product stream 380. The cumene product stream 380 is then recycled to the second separation zone 360.

The cumene stream 370 can be collected as a final product, or optionally subjected to further downstream processing. For example, the cumene stream 370 could be processed to produce phenol and acetone, if desired.

The third stream 330 enters a third separation zone 385 to separate the stream 330 into at least a di-isopropyl toluene isomers stream 390 and a cymenes stream 395. The di-isopropyl toluene isomers stream 390 is provided to a third transalkylation zone 400 to transalkylate at least a portion of the di-isopropyl toluene isomers with pure toluene in the presence of a transalkylation catalyst, forming a cymenes product stream 405. The cymenes product stream 405 is then recycled to the third separation zone 385.

The cymenes stream 395 can be collected as a final product, or optionally subjected to further downstream processing. For example, the cymenes stream 395 could be processed to produce cresols, if desired.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for producing alkylated aromatic compounds, comprising:

pyrolyzing a coal feed to produce a coke stream and a coal tar stream;

hydrotreating the coal tar stream;

cracking the hydrotreated coal tar stream;

separating a portion of the cracked coal tar stream to obtain a fraction having an initial boiling point in the range of about 60° C. to about 180° C.;

extracting an aromatics-rich hydrocarbon stream by contacting the fraction with one or more solvents;

contacting the aromatics-rich hydrocarbon stream with an alkylating agent in the presence of an alkylation catalyst in an alkylation zone to produce an alkylated aromatic stream, or contacting the aromatics-rich hydrocarbon stream with an aliphatic compound or methanol in the presence of a methylation catalyst in a methylation zone to produce a methylated aromatic stream; and separating the alkylated aromatic stream, the methylated aromatic stream, or both into at least a benzene stream, a toluene stream, and a xylenes stream.

2. The process of claim 1 further comprising recycling the benzene stream to the alkylation zone, the methylation zone, or both.

3. The process of claim 1 further comprising:
contacting the toluene stream with a $C_{9+}$ aromatic compound in the presence of a transalkylation catalyst in a toluene reaction zone to produce benzene and xylenes, or contacting the toluene stream with a methylating catalyst in a toluene reaction zone to produce benzene and xylenes, or contacting the toluene stream with a disproportionation catalyst in a toluene reaction zone to produce benzene and xylenes; and
separating the benzene and xylenes into a benzene stream and a second xylenes stream.

4. The process of claim 3 further comprising recycling the benzene stream to the alkylation zone, the methylation zone, or both.

5. The process of claim 3 further comprising:
separating at least one of para-xylene, meta-xylene, and ortho-xylene from the second xylenes stream in a xylene recovery zone to form at least one of a para-xylene stream, a meta-xylene stream, and an ortho-xylene stream, and a residual xylene stream.

6. The process of claim 1 further comprising:
separating at least one of para-xylene, meta-xylene, and ortho-xylene from the xylenes stream in a xylene recovery zone to form at least one of a para-xylene stream, a meta-xylene stream, and an ortho-xylene stream, and a residual xylene stream.

7. The process of claim 6 wherein separating at least one of para-xylene, meta-xylene, and ortho-xylene from the xylenes stream comprises separating at least one of para-xylene and meta-xylene using an adsorption process.

8. The process of claim 6 wherein separating at least one of para-xylene, meta-xylene, and ortho-xylene from the xylenes stream comprises separating ortho-xylene using a distillation process.

9. The process of claim 6 further comprising:
isomerizing the residual xylene stream;
separating the isomerized residual xylene stream in the xylene recovery zone.

10. The process of claim 1, further comprising:
separating a $C_{9+}$ aromatic stream from the alkylated aromatic stream, the methylated aromatic stream, or both;
separating $C_9$ aromatics from the $C_{9+}$ aromatic stream;
contacting the $C_9$ aromatics with a platinum-containing zeolite catalyst to convert at least a portion of the $C_9$ aromatics to trimethylbenzenes; and
introducing the trimethylbenzenes stream into the alkylation zone.

11. The process of claim 1, wherein the alkylation catalyst is an MFI zeolite catalyst.

12. The process of claim 1, wherein the one or more solvents comprises one or more of sulfolane, an organic ether of sulfolane, NMP, and NMF.

13. The process of claim 1, wherein the contacting comprises contacting the aromatic fraction with methanol, and wherein the alkylation catalyst is a strong acid catalyst.

14. The process of claim 13, wherein the strong acid catalyst is selected from the group consisting of sulfuric acid, hydrofluoric acid, or ionic liquid.

15. A process for producing alkylated aromatic compounds, comprising:

pyrolyzing a coal feed to produce a coke stream and a coal tar stream;
hydrotreating the coal tar stream;
cracking the hydrotreated coal tar stream;
separating a portion of the cracked coal tar stream to obtain a fraction having an initial boiling point in the range of about 60° C. to about 180° C.;
extracting an aromatics-rich hydrocarbon stream by contacting the fraction with one or more solvents;
contacting the aromatics-rich hydrocarbon stream with an alkylating agent in the presence of an alkylation catalyst in an alkylation zone to produce an alkylated aromatic stream, or contacting the aromatics-rich hydrocarbon stream with an aliphatic compound or methanol in the presence of a methylation catalyst in a methylation zone to produce a methylated aromatic stream; and
separating the alkylated aromatic stream into at least a first stream comprising ethyl benzene and diethyl benzenes, a second stream comprising cumenes and di-isopropyl benzenes, and a third stream comprising cymenes and di-isopropyl toluenes in a separation zone.

16. The method of claim 15 further comprising:
separating at least one of the first stream, the second stream, or the third stream into at least two fractions, the first stream being separated into an ethylbenzene stream and a diethyl benzenes stream in a first separation zone, the second stream being separated into a cumenes stream and a di-isopropyl benzenes stream in a second separation zone, and the third stream being separate into a cymenes stream and a di-isopropyl toluenes stream in a third separation zone;
transalkylating at least one of the diethyl benzenes stream, the di-isopropyl benzenes stream, or the di-isopropyl toluenes stream by:
contacting the diethyl benzenes stream with benzene or toluene in the presence of a transalkylation catalyst in a transalkylation zone to produce a mixture of ethylbenzene and diethyl benzenes;
contacting the di-isopropyl benzenes stream with benzene or toluene in the presence of a transalkylation catalyst in a transalkylation zone to produce a mixture of cumene and di-isopropyl benzenes;
contacting the di-isopropyl toluenes stream with benzene or toluene in the presence of a transalkylation catalyst in a transalkylation zone to produce a mixture of cymene and di-isopropyl benzenes.

17. The method of claim 16 further comprising:
recycling at least one of: the mixture of ethylbenzene and diethyl benzenes to the first separation zone; the mixture of cumene and di-isopropyl benzenes to the second separation zone; and the mixture of cymene and di-isopropyl benzenes to the third separation zone.

18. The method of claim 16 further comprising isomerizing the ethylbenzene stream in the presence of an isomerization catalyst in a xylene isomerization zone.

19. The method of claim 16 further comprising converting the cumenes stream to form a phenol product and an acetone product.

20. The method of claim 16 further comprising converting the cymenes stream to form a cresols product.

* * * * *